(12) United States Patent
Sheedy

(10) Patent No.: US 10,898,891 B2
(45) Date of Patent: Jan. 26, 2021

(54) PROCESS FOR STRIPPING CARBAMATE FROM ION EXCHANGE RESIN

(71) Applicant: ECO-TEC LTD., Pickering (CA)

(72) Inventor: Michael A. Sheedy, Uxbridge (CA)

(73) Assignee: ECO-TEC LTD., Pickering (CA)

( * ) Notice: Subject to any disclaimer, the term of this patent is extended or adjusted under 35 U.S.C. 154(b) by 286 days.

(21) Appl. No.: 15/753,601

(22) PCT Filed: Aug. 20, 2015

(86) PCT No.: PCT/CA2015/000471
§ 371 (c)(1),
(2) Date: Feb. 20, 2018

(87) PCT Pub. No.: WO2017/027953
PCT Pub. Date: Feb. 23, 2017

(65) Prior Publication Data
US 2019/0009268 A1   Jan. 10, 2019

(51) Int. Cl.
*B01J 49/57* (2017.01)
*B01J 41/05* (2017.01)
(Continued)

(52) U.S. Cl.
CPC .......... *B01J 49/57* (2017.01); *B01D 53/1406* (2013.01); *B01D 53/1425* (2013.01); *B01D 53/1475* (2013.01); *B01D 53/1487* (2013.01); *B01D 53/96* (2013.01); *B01J 41/05* (2017.01); *B01J 49/07* (2017.01); *C01B 21/12* (2013.01);
(Continued)

(58) Field of Classification Search
CPC ............ B01D 53/1406; B01D 53/1425; B01D 53/1456; B01D 53/1475; B01D 53/1487; B01D 2257/504; B01J 49/07; B01J 49/57; B01J 49/60
See application file for complete search history.

(56) References Cited

U.S. PATENT DOCUMENTS

| 5,788,864 A | 8/1998 | Coberly et al. |
| 6,245,128 B1 * | 6/2001 | George, Jr. ........ B01D 53/1425 |
| | | 95/186 |

(Continued)

FOREIGN PATENT DOCUMENTS

| CA | 2891175 | 5/2014 |
| CN | 101400428 A | 4/2009 |
| WO | WO 2012/100330 | 8/2012 |

OTHER PUBLICATIONS

European Search Report issued in corresponding Application No. 15901189.9 dated Mar. 4, 2019.
(Continued)

*Primary Examiner* — Jason M Greene

(57) ABSTRACT

In a preferred embodiment, there is provided a process for separating an amine compound or a conjugate acid thereof and a carbamate compound or a conjugate acid thereof from a mixture having the amine compound, the carbamate compound, carbon dioxide and at least one anionic contaminant salt using an anionic exchange column, the process including passing the mixture through the column to obtain a first effluent and passing through the column an extraction fluid to obtain a second effluent, where the extraction fluid most preferably includes carbonic acid.

22 Claims, 1 Drawing Sheet

(51) Int. Cl.
*B01J 49/07* (2017.01)
*B01D 53/96* (2006.01)
*C07D 295/023* (2006.01)
*C07D 295/088* (2006.01)
*C01B 21/12* (2006.01)
*C07D 295/205* (2006.01)
*C07D 295/13* (2006.01)
*C07C 213/10* (2006.01)
*B01D 53/14* (2006.01)
*C07C 209/86* (2006.01)
*C07C 269/08* (2006.01)

(52) U.S. Cl.
CPC .......... *C07C 209/86* (2013.01); *C07C 213/10* (2013.01); *C07C 269/08* (2013.01); *C07D 295/023* (2013.01); *C07D 295/088* (2013.01); *C07D 295/13* (2013.01); *C07D 295/205* (2013.01); *B01D 2252/20447* (2013.01); *B01D 2252/20484* (2013.01); *B01D 2257/302* (2013.01); *B01D 2257/304* (2013.01); *B01D 2257/308* (2013.01); *B01D 2257/40* (2013.01); *B01D 2257/404* (2013.01); *B01D 2257/408* (2013.01); *B01D 2257/504* (2013.01); *B01D 2258/0283* (2013.01)

(56) References Cited

U.S. PATENT DOCUMENTS

| | | | |
|---|---|---|---|
| 6,344,886 B2 | 1/2002 | Barnes, Jr. et al. | |
| 2007/0213415 A1* | 9/2007 | Sarlis | B01J 49/60 521/27 |
| 2008/0159937 A1* | 7/2008 | Ouimet | B01D 53/1475 423/230 |
| 2012/0059073 A1* | 3/2012 | Morris | B01J 49/60 521/26 |
| 2013/0192465 A1* | 8/2013 | Trofimuk | B01D 53/1425 95/179 |
| 2013/0309155 A1* | 11/2013 | Parisi | B01D 53/1425 423/229 |
| 2015/0209724 A1* | 7/2015 | Ogawa | B01D 53/1475 423/242.7 |
| 2017/0225118 A1* | 8/2017 | Kim | B01D 53/1475 |
| 2017/0312681 A1* | 11/2017 | Jurg | B01D 53/1475 |

OTHER PUBLICATIONS

Examination Report recieved from the Indian Patent Office in respect of corresponding Indian Application No. 201837003495 dated Aug. 21, 2019.
International Search Report prepared in respect of PCT/CA2015/000471, dated Dec. 9, 2015.
Written Opinion prepared in respect of PCT/CA2015/000471, dated Nov. 12, 2015.
Examination Report recieved from the Chinese Patent Office in respect of corresponding Chinese Application No. 201580082532.7 dated Jan. 7, 2020.

* cited by examiner

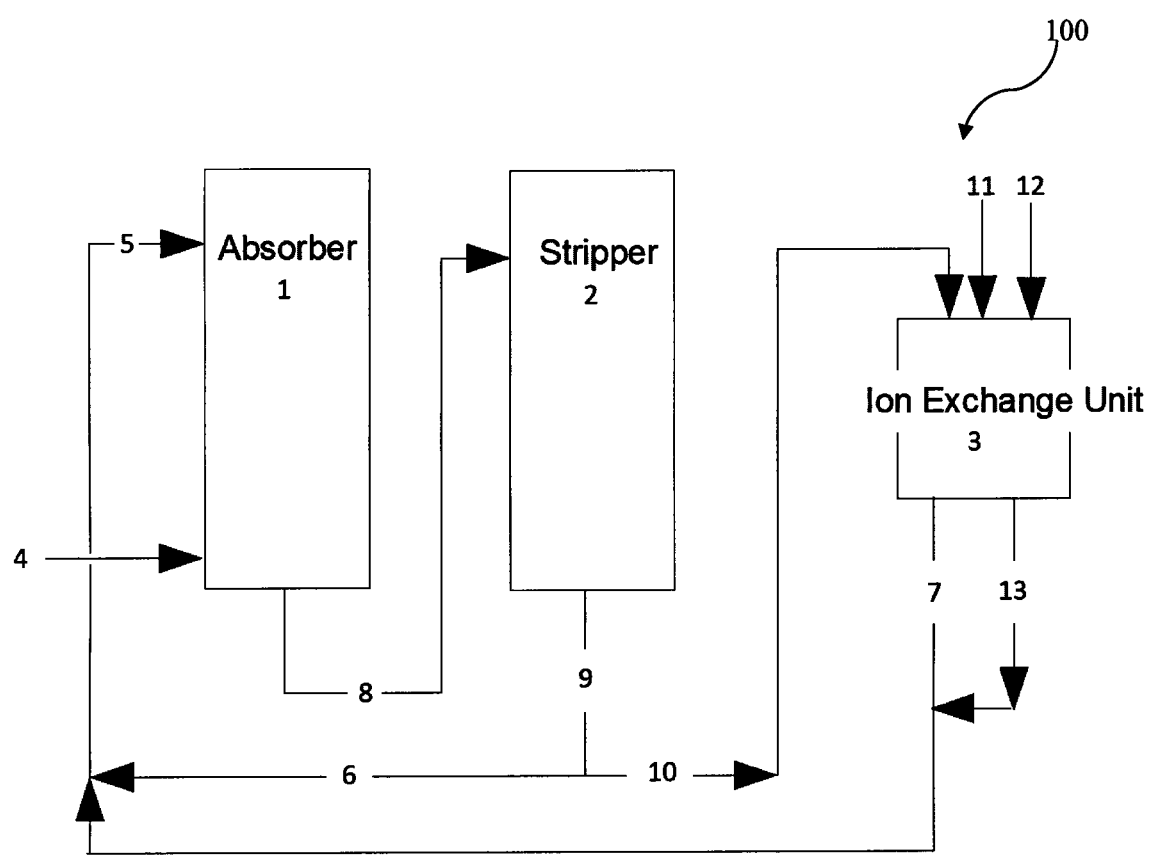

PROCESS FOR STRIPPING CARBAMATE FROM ION EXCHANGE RESIN

FIELD OF THE INVENTION

This invention relates to purification by ion exchange of a primary or secondary alkanolamine (referred hereinafter as "alkanolamine" or more broadly "amine") solution containing a high level of carbon dioxide. In particular, in a preferred embodiment this invention relates to a process for extracting an amine compound and a carbamate compound from a mixture which includes the amine and carbamate compounds and an anionic contaminant salt, where the mixture is obtained from a carbon capture process applied to for example a flue gas stream from a coal fire power plant.

BACKGROUND OF THE INVENTION

Carbon dioxide absorption by primary and secondary alkanolamines, such as monoethanolamine or "MEA" having the formula $HOCH_2CH_2NH_2$, is one of the preferred methods for carbon capture from power plant exhaust gases. The level of carbon dioxide included in an alkanolamine solution used for carbon dioxide absorption is typically described as the loading and more specifically the lean loading when it has been treated for carbon dioxide removal in a steam stripping tower. The loading concentration is expressed as moles of carbon dioxide per mole of amine in the solution. In this case, high carbon dioxide removal efficiencies from the gas stream are not required, which allows a high lean loading that may range from 0.05 to 0.3 mol/mol. Primary and secondary amines may react with carbon dioxide to form anionic carbamates. For instance, monoethanolamine may react with carbon dioxide to form $HOCH_2CH_2NHCOO^-$ according to the following reaction (1):

It is to be appreciated that any chemical equation or reaction identified herein with a forward arrow is not strictly intended to indicate the chemical reaction as being an irreversible reaction, and that with an equilibrium arrow a reversible reaction. Any forward or equilibrium arrows used herein are merely intended to distinguish between reactants and products of a chemical reaction, and not whether the chemical reaction is reversible or irreversible, unless expressly indicated for the specific chemical reaction as being reversible or irreversible.

Alkanolamine solutions are subject to chemical degradation and contamination that results in the production and accumulation of corrosive heat stable salts such as formate, $HCOO^-$. To minimize corrosion, the anions of these salts can be removed by the use of anion exchange resin processes such as that described in U.S. Pat. No. 5,277,822. The heat stable salt ion exchange process occurs according to equation (2), where $R$—$N^+$ represents an anion resin exchange site:

Normally the heat stable salts need to be maintained at a level of 0.5% w/w to minimize corrosion. In a similar manner the carbamate ion, $HOCH_2CH_2NHCOO^-$ will also exchange onto the anion resin according to equation (3):

Typical carbamate concentrations in solutions used for carbon capture range from 1.5 to 4.5% w/w. At such a relatively high concentration, a significant amount of carbamate loads onto the anion exchange resin.

The heat stable salt anion is removed from the anion exchange resin using a regenerant solution that is typically sodium hydroxide or NaOH. Regeneration is not selective for heat stable salts and will also remove the carbamate according to equations (4) and (5):

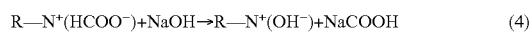

The regenerated heat stable salt and carbamate are flushed away from the resin in a spent regenerant and rinse stream that is sent to waste. Loss of the alkanolamine incorporated in the carbamate represents an operating cost. This loss also contaminates the waste stream by increasing the chemical oxygen demand and the total nitrogen concentrations. This may increase the load on the power station waste water treatment plant or may cause the permitted discharge allowance to be exceeded. To avoid this loss of alkanolamine and contamination of the waste regenerant and rinse stream there is a need for a method of removing the carbamate from the ion exchange resin before the regeneration process.

SUMMARY OF THE INVENTION

One possible non-limiting object of the present invention is to provide a process which may permit for reduction of the amount of an alkanolamine compound lost to a waste regenerant stream of an ion exchange process that is treating a fluid containing an alkanolamine compound used to absorb carbon dioxide.

Another possible non-limiting object of the present invention is to provide a process for removing a carbamate compound from an anion exchange resin prior to regeneration of the resin, and which may incorporate an acid fluid contacting step to decompose the carbamate compound to produce an alkanolamine compound and carbon dioxide.

Another possible non-limiting object of the present invention is to provide a process for extracting a carbamate compound and/or an amine compound in industrial carbon capture, and which may be integrated into an existing industrial system or facilities without necessarily requiring significant reconstruction or reconfiguration.

In one aspect, the present invention provides a process for separating an amine compound or a conjugate acid thereof and a carbamate compound or a conjugate acid thereof from a mixture having the amine compound, the carbamate compound, carbon dioxide and at least one anionic contaminant salt using an anionic exchange column having a plurality of anion exchange sites, the amine compound being an optionally substituted piperazine or having formula (1) of $R_{3-x}N(R^1\text{-}Q\text{-}R^1\text{—}OH)_x$ and the carbamate compound being an optionally substituted piperazine carbamate or piperazine dicarbamate, or having formula (2) of $(HO\text{—}R^1\text{-}Q\text{-}R^1)_y NH_{2-y}C(O)O^-$, wherein at least a portion of the carbamate compound is present in the mixture from a reversible reaction between the amine compound and the carbon dioxide to produce the carbamate compound and a hydrogen atom or the conjugate acid of the amine compound, wherein x and y are independently of each other 1 or 2, R is a hydrogen atom or optionally substituted straight or branched $C_1$-$C_8$ alkyl, $R^1$ is nothing or optionally substituted straight or branched $C_1$-$C_4$ alkylene, and Q is nothing, O or S, and wherein the optionally substituted piperazine comprises at least one ring nitrogen atom bonded to a hydrogen atom, at least one R is a hydrogen atom, and at least $R^1$ in each said formulas (1) and (2) is optionally substituted straight or branched $C_1$-$C_4$ alkylene; wherein the process comprises: passing the mixture through the column to effect attachment of the at least one anionic contaminant salt to the anion exchange sites, and collecting from the column a first effluent comprising at least the amine compound or the conjugate acid thereof; passing through the column an extraction fluid to obtain a second effluent, the extraction fluid comprising an acid compound having one or more of carbonic acid, hydrochloric acid, sulfuric acid, citric acid, acetic acid and sulfamic acid selected to effect removal of the carbamate compound attached to the anion exchange sites, wherein the second effluent comprises at least the carbamate compound, the conjugate acid of the carbamate compound or a decomposition product thereof, said decomposition product comprising the amine compound and the carbon dioxide; and passing through the column a regeneration fluid to regenerate the column, the regeneration fluid comprising an anionic regeneration compound selected to replace the anionic contaminant salt attached to the anion exchange sites, wherein the first and second effluents are collected to obtain a separated mixture comprising at least the amine compound or the conjugate acid thereof and the carbamate compound or the conjugate acid thereof.

In another aspect, the present invention provides a process for separating an amine compound or a conjugate acid thereof and a carbamate compound or a conjugate acid thereof from a mixture having the amine compound, the carbamate compound, carbon dioxide and at least one anionic contaminant salt using an anionic exchange column having a plurality of anion exchange sites, the amine compound being an optionally substituted piperazine or having formula (1) of $R_{3-x}N(R^1$-Q-$R^1$—OH$)_x$ and the carbamate compound being an optionally substituted piperazine carbamate or piperazine dicarbamate, or having formula (2) of (HO—$R^1$-Q-$R^1)_y$NH$_{2-y}$C(O)O$^-$, wherein x and y are independently of each other 1 or 2, R is a hydrogen atom or optionally substituted straight or branched $C_1$-$C_8$ alkyl, $R^1$ is nothing or optionally substituted straight or branched $C_1$-$C_4$ alkylene, and Q is nothing, O or S, and wherein the optionally substituted piperazine comprises at least one ring nitrogen atom bonded to a hydrogen atom, at least one R is a hydrogen atom, and at least $R^1$ in each said formulas (1) and (2) is optionally substituted straight or branched $C_1$-$C_4$ alkylene; wherein the process comprises: passing the mixture through the column to effect attachment of the at least one anionic contaminant salt to the anion exchange sites, and collecting from the column a first effluent comprising at least the amine compound or the conjugate acid thereof; passing through the column an extraction fluid to obtain a second effluent, the extraction fluid comprising an acid compound selected to effect removal of the carbamate compound attached to the anion exchange sites, wherein the second effluent comprises at least the carbamate compound, the conjugate acid of the carbamate compound or a decomposition product thereof, said decomposition product comprising the amine compound and the carbon dioxide; and passing through the column a regeneration fluid to regenerate the column, the regeneration fluid comprising an anionic regeneration compound selected to replace the anionic contaminant salt attached to the anion exchange sites, wherein the first and second effluents are collected to obtain a separated mixture comprising at least the amine compound or the conjugate acid thereof and the carbamate compound or the conjugate acid thereof.

In yet another aspect, the present invention provides a process for reducing an amount of carbon dioxide in a gaseous stream comprising the carbon dioxide and optionally one or more of hydrogen sulfide, sulfur dioxide, carbonyl sulfide, carbon disulfide, nitrogen dioxide and hydrogen cyanide, the process comprising contacting the gaseous stream with a liquid stream comprising an amine compound of formula (3) HO—$R^2$—NH$_2$ to obtain a loaded fluid mixture and treating the loaded fluid mixture, wherein $R^2$ is straight or branched $C_1$-$C_8$ alkylene, wherein said treating the loaded fluid mixture comprises heating the loaded fluid mixture with a steam to remove at least a portion of the gaseous stream absorbed in the loaded fluid mixture to obtain a heated fluid mixture and refluxing the heated fluid mixture to obtain an aqueous solution, the aqueous solution comprising the amine compound, the carbon dioxide, a carbamate compound and an anionic contaminant salt, wherein the carbamate compound is present in the aqueous solution from the reversible reaction 2 HO—$R^2$—NH$_2$+CO$_2$ ⇌ HO—$R^2$—NH$_3^+$+HO—$R^2$—NH—COO$^-$, and the anionic contaminant salt is produced during one or both of said contacting the gaseous stream with the liquid stream and said heating the loaded fluid mixture with the steam, wherein the process further comprises separating the amine compound or a conjugate acid thereof and the carbamate compound or a conjugate acid thereof from the aqueous solution using an anionic exchange column having a plurality of anion exchange sites, said separating comprising: passing the aqueous solution through the column to effect attachment of the anionic contaminant salt to the anion exchange sites, and collecting from the column a first effluent comprising at least the amine compound or the conjugate acid thereof; and passing through the column an extraction fluid to obtain a second effluent, the extraction fluid comprising an acid compound having one or more of carbonic acid, hydrochloric acid, sulfuric acid, citric acid, acetic acid and sulfamic acid selected to effect removal of the carbamate compound attached to the anion exchange sites, wherein the second effluent comprises at least the carbamate compound, the conjugate acid of the carbamate compound or a decomposition product thereof, said decomposition product comprising the amine compound and the carbon dioxide; wherein the first and second effluents are collected to obtain a separated mixture comprising at least the amine compound or the conjugate acid thereof and the carbamate compound or the conjugate acid thereof, said separated mixture being for addition to the liquid stream.

It is to be appreciated that the process of the current invention may be practiced alone or as part of a method for removing or reducing carbon dioxide in a gas or gas mixture, such as but not limited to carbon capture for an exhaust gas produced by a fossil fuel power plant or an industrial facility powered by fossil fuel combustion. The fossil fuel power plant preferably includes a coal burning power station. In one embodiment, the process is for use with a method for removing from a gaseous stream carbon dioxide and optionally one or more of hydrogen sulfide, sulfur dioxide, carbonyl sulfide, carbon disulfide, nitrogen dioxide and hydrogen cyanide, said mixture being an aqueous solution obtained from contacting a liquid stream comprising the amine compound with the gaseous stream to obtain a loaded fluid mixture, heating the loaded fluid mixture with a steam to remove at least a portion of the gaseous stream absorbed in the loaded fluid mixture to obtain a heated fluid mixture, and refluxing the heated fluid mixture to obtain the aqueous solution.

It is to be appreciated that a carbon dioxide loading capacity of the aqueous solution, as may be measured by a molar ratio between carbon dioxide and the amine compound, may be affected by a number of different parameters and factors, such as the identity of the amine compound included in the aqueous solution. In one embodiment, the aqueous solution has a carbon dioxide loading capacity between about 0.01 and about 1.0, preferably between about 0.05 and about 0.3, or more preferably between about 0.1 and about 0.15, said loading capacity being obtained from a molar ratio between the carbon dioxide and the amine compound in the aqueous solution. In one embodiment, the aqueous solution has a concentration of the carbamate compound between about 0.5 weight % and about 10 weight %, preferably between about 1.0 weight % and about 8 weight %, or more preferably between about 1.5 weight % and 4.5 weight % with respect to the total weight of the aqueous solution.

To protect the anion exchange column and reduce degradation of the column or resin material, the mixture or aqueous solution is preferably below 60° C. prior to passing through the column. In one embodiment, prior to said passing the mixture through the column, the aqueous solution has a temperature between about 10° C. and about 50° C., preferably between about 20° C. and about 40° C., or more preferably between about 30° C. and about 38° C., and optionally is filtered to remove an insoluble precipitate. The insoluble precipitate may include for example but not limited to iron(II) sulfide produced from a reaction between dissolved iron and sulfide ions present in the mixture, and which may be present in the form of a fine black precipitate.

Although not wishing to be bound by theory, it has been appreciated that heat stable salts may be produced during carbon capture as a result of degradation or thermal degradation of an amine compound used for carbon dioxide absorption. Such heat stable salts may be corrosive, and if not removed, could cause structural damages to various components of a system utilized for carbon capture. In one embodiment, at least a portion of the at least one anionic contaminant salt is produced during one or both of said contacting the liquid stream with the gaseous stream and said heating the loaded fluid mixture with the steam, said at least one anionic contaminant salt being a heat stable salt comprising one or more of a formate salt, an acetate salt, a thiocyanate salt, a thiosulfate salt, a glycolate salt, a chloride salt, an oxalate salt, a butyrate salt, a phosphate salt, a nitrate salt, a propionate salt and a sulfate salt, or preferably a formate salt. In one embodiment, the heat stable salt comprises one or more of acetic acid, ammonium thiocyanate, ammonium thiosulfate, formic acid, glycolic acid, hydrochloric acid, malonic acid, oxalic acid, sodium chloride, sodium thiocyanate, sodium thiosulfate, succinic acid, sulfuric acid and sulfurous acid. It has been envisioned that the process of the current invention may be utilized for removal or reduction of such salts during carbon capture, while reducing an amount of the amine compound lost during the salt removal/reduction.

In one embodiment, said passing the extraction fluid through the column is conducted at a pressure between about 0.5 atm and about 20 atm, preferably between about 1 atm and about 15 atm, or more preferably between about 6 atm and about 8 atm.

In one embodiment, the amine compound is one or more of monoethanolamine, diethanolamine, monoisopropanolamine, diisopropanolamine, 1-amino-2-propanol, 2-amino-2-methyl-1-propanol, 2-amino-2-methyl-1,3-propanediol, N-methylmonoethanolamine, N-ethylmonoethanolamine, N-butylmonoethanolamine, 2-(2-aminoethoxy) ethanol, N-(2-hydroxyethyl)ethylenediamine, piperazine, 1-[2-(2-Hydroxyethoxy)ethyl]piperazine, 1-methylpiperazine, 1-(2-methoxyethyl)piperazine, 1-(2-hydroxyethyl)piperazine, 1-(2-ethoxyethyl)piperazine and 1-(2-aminoethyl) piperazine, or more preferably monoethanolamine. In one embodiment, the optionally substituted piperazine is one or more of 1-(2-hydroxyethyl)piperazine, 1-(2-aminoethyl) piperazine, 1-(2-ethoxyethyl)piperazine, 1-(2-methoxyethyl)piperazine, 1-(1,3-dioxolan-2-ylmethyl)piperazine, 1-(1-methyl-4-piperidinyl)piperazine, 1-[2-(2-hydroxyethoxy)ethyl]piperazine, 1-[2-(dimethylamino)ethyl]piperazine, 1-[3-(dimethylamino)propyl]piperazine, 1-methylpiperazine, 1-ethylpiperazine, 1-butylpiperazine, 1-decylpiperazine and 1-(4-hydroxybutyl)piperazine.

In one embodiment, the amine compound has formula (3) $HO-R^2-NH_2$, $R^2$ being $C_1$-$C_8$ alkylene, and the reversible reaction is $2\ HO-R^2-NH_2 + CO_2 \rightleftharpoons HO-R^2-NH_3^+ + HO-R^2-NH-COO^-$, and wherein the acid compound comprises carbonic acid, the carbonic acid being selected to donate a proton to $HO-R^2-NH-COO^-$ attached to the anion exchange sites to form $HO-R^2-NH-COOH$ and a bicarbonate ion, and optionally decompose $HO-R^2-NH-COOH$ to $HO-R^2-NH_2$ and $CO_2$.

In one embodiment, at least a portion of the carbamate compound is present in the mixture from a reversible reaction between the amine compound and the carbon dioxide to produce the carbamate compound and a hydrogen atom or the conjugate acid of the amine compound, and the amine compound has formula (3) $HO-R^2-NH_2$, $R^2$ being $C_1$-$C_8$ alkylene, wherein the reversible reaction is $2\ HO-R^2-NH_2 + CO_2 \rightleftharpoons HO-R^2-NH_3^+ + HO-R^2-NH-COO^-$, and the acid compound comprises carbonic acid, the carbonic acid being selected to donate a proton to $HO-R^2-NH-COO^-$ attached to the anion exchange sites to form $HO-R^2-NH-COOH$ and a bicarbonate ion, and optionally decompose $HO-R^2-NH-COOH$ to $HO-R^2-NH_2$ and $CO_2$.

It is to be appreciated that the acid compound is not particularly limited, provided that the acid compound may permit for preferential removal of the carbamate compound from the anion exchange resin when compared to that of the anionic contaminant salt. In one embodiment, the acid compound includes one or both of a weak acid and a strong acid or preferably a weak acid. In one embodiment, the acid compound is selected to donate a proton to the carbamate compound attached to the anion exchange sites to form the conjugate acid of the carbamate compound and optionally to decompose the conjugate acid of the carbamate compound to form the amine compound, thereby removing the carbamate compound from the anion exchange sites. In one embodiment, the acid compound comprises one or more of carbonic acid, hydrochloric acid, sulfuric acid, citric acid, acetic acid and sulfamic acid, or preferably carbonic acid. Most preferably, the acid compound is carbonic acid. In a preferred embodiment, the carbonic acid is selected to donate a proton to the carbamate compound attached to the anion exchange sites to form the conjugate acid of the carbamate compound and a bicarbonate ion, and to decompose the conjugate acid of the carbamate compound to the amine compound and the carbon dioxide.

In one embodiment, the regeneration fluid is an aqueous solution comprising one or more of sodium hydroxide, sodium carbonate and sodium bicarbonate, or preferably sodium hydroxide at a concentration between about 10 g/L and about 150 g/L, preferably between about 50 g/L and about 100 g/L, or more preferably about 80 g/L.

In one embodiment, the separated mixture is a separated aqueous solution having the at least one anionic contaminant salt at a concentration up to about 3 weight %, preferably up to about 1 weight % or more preferably up to about 0.5 weight % with respect to the total weight of the separated aqueous solution.

In one embodiment, the anionic exchange column comprises a type 1 or 2 strong base anion resin, and each said anion exchange sites comprise a quaternary amino moiety.

In one embodiment, said separating further comprises passing through the column a regeneration fluid to regenerate the column, the regeneration fluid comprising an anionic regeneration compound selected to replace the anionic contaminant salt attached to the anion exchange sites, wherein the regeneration fluid comprises one or more of sodium hydroxide, sodium carbonate and sodium bicarbonate, or preferably sodium hydroxide at a concentration between about 10 g/L and about 150 g/L, preferably between about 50 g/L and about 100 g/L, or more preferably about 80 g/L.

In aspect (1), the present invention provides a process for separating an amine compound or a conjugate acid thereof and a carbamate compound or a conjugate acid thereof from a mixture having the amine compound, the carbamate compound, carbon dioxide and at least one anionic contaminant salt using an anionic exchange column having a plurality of anion exchange sites, the amine compound being an optionally substituted piperazine or having formula (1) of $R_{3-x}N(R^1\text{-}Q\text{-}R^1\text{---}OH)_x$ and the carbamate compound being an optionally substituted piperazine carbamate or piperazine dicarbamate, or having formula (2) of $(HO\text{---}R^1\text{-}Q\text{-}R^1)_y$, $NH_{2-y}C(O)O^-$, wherein at least a portion of the carbamate compound is present in the mixture from a reversible reaction between the amine compound and the carbon dioxide to produce the carbamate compound and a hydrogen atom or the conjugate acid of the amine compound, wherein x and y are independently of each other 1 or 2, R is a hydrogen atom or optionally substituted straight or branched $C_1$-$C_8$ alkyl, $R^1$ is nothing or optionally substituted straight or branched $C_1$-$C_4$ alkylene, and Q is nothing, O or S, and wherein the optionally substituted piperazine comprises at least one ring nitrogen atom bonded to a hydrogen atom, at least one R is a hydrogen atom, and at least $R^1$ in each said formulas (1) and (2) is optionally substituted straight or branched $C_1$-$C_4$ alkylene; wherein the process comprises: passing the mixture through the column to effect attachment of the at least one anionic contaminant salt to the anion exchange sites, and collecting from the column a first effluent comprising at least the amine compound or the conjugate acid thereof; passing through the column an extraction fluid to obtain a second effluent, the extraction fluid comprising an acid compound having one or more of carbonic acid, hydrochloric acid, sulfuric acid, citric acid, acetic acid and sulfamic acid selected to effect removal of the carbamate compound attached to the anion exchange sites, wherein the second effluent comprises at least the carbamate compound, the conjugate acid of the carbamate compound or a decomposition product thereof, said decomposition product comprising the amine compound and the carbon dioxide; and passing through the column a regeneration fluid to regenerate the column, the regeneration fluid comprising an anionic regeneration compound selected to replace the anionic contaminant salt attached to the anion exchange sites, wherein the first and second effluents are collected to obtain a separated mixture comprising at least the amine compound or the conjugate acid thereof and the carbamate compound or the conjugate acid thereof.

In aspect (2), the present invention provides a process for separating an amine compound or a conjugate acid thereof and a carbamate compound or a conjugate acid thereof from a mixture having the amine compound, the carbamate compound, carbon dioxide and at least one anionic contaminant salt using an anionic exchange column having a plurality of anion exchange sites, the amine compound being an optionally substituted piperazine or having formula (1) of $R_{3-x}N(R^1\text{-}Q\text{-}R^1\text{---}OH)_x$ and the carbamate compound being an optionally substituted piperazine carbamate or piperazine dicarbamate, or having formula (2) of $(HO\text{---}R^1\text{-}Q\text{-}R^1)_y$, $NH_{2-y}C(O)O^-$, wherein x and y are independently of each other 1 or 2, R is a hydrogen atom or optionally substituted straight or branched $C_1$-$C_8$ alkyl, $R^1$ is nothing or optionally substituted straight or branched $C_1$-$C_4$ alkylene, and Q is nothing, O or S, and wherein the optionally substituted piperazine comprises at least one ring nitrogen atom bonded to a hydrogen atom, at least one R is a hydrogen atom, and at least $R^1$ in each said formulas (1) and (2) is optionally substituted straight or branched $C_1$-$C_4$ alkylene; wherein the process comprises: passing the mixture through the column to effect attachment of the at least one anionic contaminant salt to the anion exchange sites, and collecting from the column a first effluent comprising at least the amine compound or the conjugate acid thereof; passing through the column an extraction fluid to obtain a second effluent, the extraction fluid comprising an acid compound selected to effect removal of the carbamate compound attached to the anion exchange sites, wherein the second effluent comprises at least the carbamate compound, the conjugate acid of the carbamate compound or a decomposition product thereof, said decomposition product comprising the amine compound and the carbon dioxide; and passing through the column a regeneration fluid to regenerate the column, the regeneration fluid comprising an anionic regeneration compound selected to replace the anionic contaminant salt attached to the anion exchange sites, wherein the first and second effluents are collected to obtain a separated mixture comprising at least the amine compound or the conjugate acid thereof and the carbamate compound or the conjugate acid thereof.

In aspect (3), the present invention provides a process for reducing an amount of carbon dioxide in a gaseous stream comprising the carbon dioxide and optionally one or more of hydrogen sulfide, sulfur dioxide, carbonyl sulfide, carbon disulfide, nitrogen dioxide and hydrogen cyanide, the process comprising contacting the gaseous stream with a liquid stream comprising an amine compound of formula (3) $HO\text{---}R^2\text{---}NH_2$ to obtain a loaded fluid mixture and treating the loaded fluid mixture, wherein $R^2$ is straight or branched $C_1$-$C_8$ alkylene, wherein said treating the loaded fluid mixture comprises heating the loaded fluid mixture with a steam to remove at least a portion of the gaseous stream absorbed in the loaded fluid mixture to obtain a heated fluid mixture and refluxing the heated fluid mixture to obtain an aqueous solution, the aqueous solution comprising the amine compound, the carbon dioxide, a carbamate compound and an anionic contaminant salt, wherein the carbamate compound is present in the aqueous solution from the reversible reaction 2 $HO\text{---}R^2\text{---}NH_2 + CO_2 \rightleftharpoons HO\text{---}R^2\text{---}NH_3^+ + HO\text{---}R^2\text{---}NH\text{---}COO^-$, and the anionic contaminant salt is produced during one or both of said contacting the gaseous stream with the liquid stream and said heating the loaded fluid mixture with the steam, wherein the process further comprises separating the amine compound or a conjugate acid thereof and the carbamate compound or a conjugate acid thereof from the aqueous solution using an anionic exchange column having a plurality of anion exchange sites, said separating comprising: passing the aqueous solution through the column to effect attachment of the anionic contaminant salt to the anion exchange sites, and collecting from the column a first effluent comprising at least the amine compound or the conjugate acid thereof; and passing through the column an extraction fluid to obtain a second effluent, the extraction fluid comprising an acid compound having one or more of carbonic acid, hydrochloric acid, sulfuric acid, citric acid, acetic acid and sulfamic acid selected to effect removal of the carbamate compound attached to the anion exchange sites, wherein the second effluent comprises at least the carbamate compound, the conjugate acid of the carbamate compound or a decomposition product thereof, said decomposition product comprising the amine compound and the carbon dioxide; wherein the first and second effluents are collected to obtain a separated mixture comprising at least the amine compound or the conjugate acid thereof and the carbamate compound or the conjugate acid thereof, said separated mixture being for addition to the liquid stream.

In aspect (4), the present invention provides a process according to any one or more of aspects (1) to (3) in any combination, wherein the process is for use with a method for removing from a gaseous stream carbon dioxide and optionally one or more of hydrogen sulfide, sulfur dioxide, carbonyl sulfide, carbon disulfide, nitrogen dioxide and hydrogen cyanide, said mixture being an aqueous solution obtained from contacting a liquid stream comprising the amine compound with the gaseous stream to obtain a loaded fluid mixture, heating the loaded fluid mixture with a steam to remove at least a portion of the gaseous stream absorbed in the loaded fluid mixture to obtain a heated fluid mixture, and refluxing the heated fluid mixture to obtain the aqueous solution.

In aspect (5), the present invention provides a process according to any one or more of aspects (1) to (4) in any combination, wherein the aqueous solution has a carbon dioxide loading capacity between about 0.01 and about 1.0, preferably between about 0.05 and about 0.3, or more preferably between about 0.1 and about 0.15, said loading capacity being obtained from a molar ratio between the carbon dioxide and the amine compound in the aqueous solution, and wherein the aqueous solution has a concentration of the carbamate compound between about 0.5 weight % and about 10 weight %, preferably between about 1.0 weight % and about 8 weight %, or more preferably between about 1.5 weight % and 4.5 weight % with respect to the total weight of the aqueous solution.

In aspect (6), the present invention provides a process according to any one or more of aspects (1) to (5) in any combination, wherein prior to said passing the mixture through the column, the aqueous solution has a temperature between about 10° C. and about 50° C., preferably between about 20° C. and about 40° C., or more preferably between about 30° C. and about 38° C., and optionally is filtered to remove an insoluble precipitate.

In aspect (7), the present invention provides a process according to any one or more of aspects (1) to (6) in any combination, wherein at least a portion of the at least one anionic contaminant salt is produced during one or both of said contacting the liquid stream with the gaseous stream and said heating the loaded fluid mixture with the steam, said at least one anionic contaminant salt being a heat stable salt comprising one or more of a formate salt, an acetate salt, a thiocyanate salt, a thiosulfate salt, a glycolate salt, a chloride salt, an oxalate salt, a butyrate salt, a phosphate salt, a nitrate salt, a propionate salt and a sulfate salt, or preferably a formate salt.

In aspect (8), the present invention provides a process according to any one or more of aspects (1) to (7) in any combination, wherein said passing the extraction fluid through the column is conducted at a pressure between about 0.5 atm and about 20 atm, preferably between about 1 atm and about 15 atm, or more preferably between about 6 atm and about 8 atm.

In aspect (9), the present invention provides a process according to any one or more of aspects (1) to (8) in any combination, wherein the amine compound is one or more of monoethanolamine, diethanolamine, monoisopropanolamine, diisopropanolamine, 1-amino-2-propanol, 2-amino-2-methyl-1-propanol, 2-amino-2-methyl-1,3-propanediol, N-methylmonoethanolamine, N-ethylmonoethanolamine, N-butylmonoethanolamine, 2-(2-aminoethoxy)ethanol, N-(2-hydroxyethyl)ethylenediamine, piperazine, 1-[2-(2-Hydroxyethoxy)ethyl]piperazine, 1-methylpiperazine, 1-(2-methoxyethyl)piperazine, 1-(2-hydroxyethyl)piperazine, 1-(2-ethoxyethyl)piperazine and 1-(2-aminoethyl)piperazine, or more preferably monoethanolamine.

In aspect (10), the present invention provides a process according to any one or more of aspects (1) to (9) in any combination, wherein the acid compound is selected to donate a proton to the carbamate compound attached to the anion exchange sites to form the conjugate acid of the carbamate compound and optionally to decompose the conjugate acid of the carbamate compound to form the amine compound, thereby removing the carbamate compound from the anion exchange sites.

In aspect (11), the present invention provides a process according to any one or more of aspects (1) to (10) in any combination, wherein the amine compound has formula (3) $HO-R^2-NH_2$, $R^2$ being $C_1$-$C_8$ alkylene, and the reversible reaction is $2\ HO-R^2-NH_2 + CO_2 \rightleftharpoons HO-R^2-NH_3^+ + HO-R^2-NH-COO^-$, and wherein the acid compound comprises carbonic acid, the carbonic acid being selected to donate a proton to $HO-R^2-NH-COO^-$ attached to the anion exchange sites to form $HO-R^2-NH-COOH$ and a bicarbonate ion, and optionally decompose $HO-R^2-NH-COOH$ to $HO-R^2-NH_2$ and $CO_2$.

In aspect (12), the present invention provides a process according to any one or more of aspects (1) to (11) in any combination, wherein the acid compound is carbonic acid.

In aspect (13), the present invention provides a process according to any one or more of aspects (1) to (12) in any combination, wherein the regeneration fluid is an aqueous solution comprising one or more of sodium hydroxide, sodium carbonate and sodium bicarbonate, or preferably sodium hydroxide at a concentration between about 10 g/L and about 150 g/L, preferably between about 50 g/L and about 100 g/L, or more preferably about 80 g/L.

In aspect (14), the present invention provides a process according to any one or more of aspects (1) to (13) in any combination, wherein the separated mixture is a separated aqueous solution having the at least one anionic contaminant salt at a concentration up to about 3 weight %, preferably up to about 1 weight % or more preferably up to about 0.5 weight % with respect to the total weight of the separated aqueous solution.

In aspect (15), the present invention provides a process according to any one or more of aspects (1) to (14) in any combination, wherein the anionic exchange column comprises a type 1 or 2 strong base anion resin, and each said anion exchange sites comprise a quaternary amino moiety.

In aspect (16), the present invention provides a process according to any one or more of aspects (1) to (15) in any combination, wherein the acid compound is selected to donate a proton to the carbamate compound attached to the anion exchange sites to form the conjugate acid of the carbamate compound, thereby removing the carbamate compound from the anion exchange sites.

In aspect (17), the present invention provides a process according to any one or more of aspects (1) to (16) in any combination, wherein the process is for use with a method for removing from a gaseous stream carbon dioxide and optionally one or more of hydrogen sulfide, sulfur dioxide, carbonyl sulfide, carbon disulfide, nitrogen dioxide and hydrogen cyanide, said mixture being an aqueous solution obtained from contacting a liquid stream comprising the amine compound with the gaseous stream to obtain a loaded fluid mixture, heating the loaded fluid mixture with a steam to remove at least a portion of the gaseous stream absorbed in the loaded fluid mixture to obtain a heated fluid mixture, and refluxing the heated fluid mixture to obtain the aqueous solution.

In aspect (18), the present invention provides a process according to any one or more of aspects (1) to (17) in any combination, wherein the aqueous solution has a carbon dioxide loading capacity between about 0.01 and about 1.0, preferably between about 0.05 and about 0.3, or more preferably between about 0.1 and about 0.15, said loading capacity being obtained from a molar ratio between the carbon dioxide and the amine compound in the aqueous solution, and wherein the aqueous solution has a concentration of the carbamate compound between about 0.5 weight % and about 10 weight %, preferably between about 1.0 weight % and about 8 weight %, or more preferably between about 1.5 weight % and 4.5 weight % with respect to the total weight of the aqueous solution.

In aspect (19), the present invention provides a process according to any one or more of aspects (1) to (18) in any combination, wherein prior to said passing the mixture through the column, the aqueous solution has a temperature between about 10° C. and about 50° C., preferably between about 20° C. and about 40° C., or more preferably between about 30° C. and about 38° C., and optionally is filtered to remove an insoluble precipitate.

In aspect (20), the present invention provides a process according to any one or more of aspects (1) to (19) in any combination, wherein at least a portion of the at least one anionic contaminant salt is produced during one or both of said contacting the liquid stream with the gaseous stream and said heating the loaded fluid mixture with the steam, said at least one anionic contaminant salt being a heat stable salt comprising one or more of a formate salt, an acetate salt, a thiocyanate salt, a thiosulfate salt, a glycolate salt, a chloride salt, an oxalate salt, a butyrate salt, a phosphate salt, a nitrate salt, a propionate salt and a sulfate salt, or preferably a formate salt.

In aspect (21), the present invention provides a process according to any one or more of aspects (1) to (20) in any combination, wherein said passing the extraction fluid through the column is conducted at a pressure between about 0.5 atm and about 20 atm, preferably between about 1 atm and about 15 atm, or more preferably between about 6 atm and about 8 atm.

In aspect (22), the present invention provides a process according to any one or more of aspects (1) to (21) in any combination, wherein the amine compound is one or more of monoethanolamine, diethanolamine, monoisopropanolamine, diisopropanolamine, 1-amino-2-propanol, 2-amino-2-methyl-1-propanol, 2-amino-2-methyl-1,3-propanediol, N-methylmonoethanolamine, N-ethylmonoethanolamine, N-butylmonoethanolamine, 2-(2-aminoethoxy)ethanol, N-(2-hydroxyethyl)ethylenediamine, piperazine, 1-[2-(2-Hydroxyethoxy)ethyl]piperazine, 1-methylpiperazine, 1-(2-methoxyethyl)piperazine, 1-(2-hydroxyethyl)piperazine, 1-(2-ethoxyethyl)piperazine and 1-(2-aminoethyl)piperazine, or more preferably monoethanolamine.

In aspect (23), the present invention provides a process according to any one or more of aspects (1) to (22) in any combination, wherein the acid compound comprises one or more of carbonic acid, hydrochloric acid, sulfuric acid, citric acid, acetic acid and sulfamic acid, or preferably carbonic acid.

In aspect (24), the present invention provides a process according to any one or more of aspects (1) to (23) in any combination, wherein at least a portion of the carbamate compound is present in the mixture from a reversible reaction between the amine compound and the carbon dioxide to produce the carbamate compound and a hydrogen atom or the conjugate acid of the amine compound, and the amine compound has formula (3) $HO-R^2-NH_2$, $R^2$ being $C_1$-$C_8$ alkylene, wherein the reversible reaction is $2\ HO-R^2-NH_2 + CO_2 \rightleftharpoons HO-R^2-NH_3^+ + HO-R^2-NH-COO^-$, and the acid compound comprises carbonic acid, the carbonic acid being selected to donate a proton to $HO-R^2-NH-COO^-$ attached to the anion exchange sites to form $HO-R^2-NH-COOH$ and a bicarbonate ion, and optionally decompose $HO-R^2-NH-COOH$ to $HO-R^2-NH_2$ and $CO_2$.

In aspect (25), the present invention provides a process according to any one or more of aspects (1) to (24) in any combination, wherein the acid compound is carbonic acid.

In aspect (26), the present invention provides a process according to any one or more of aspects (1) to (25) in any combination, wherein the regeneration fluid is an aqueous solution comprising one or more of sodium hydroxide, sodium carbonate and sodium bicarbonate, or preferably sodium hydroxide at a concentration between about 10 g/L and about 150 g/L, preferably between about 50 g/L and about 100 g/L, or more preferably about 80 g/L.

In aspect (27), the present invention provides a process according to any one or more of aspects (1) to (26) in any combination, wherein the separated mixture is a separated aqueous solution having the at least one anionic contaminant salt at a concentration up to about 3 weight %, preferably up to about 1 weight % or more preferably up to about 0.5 weight % with respect to the total weight of the separated aqueous solution.

In aspect (28), the present invention provides a process according to any one or more of aspects (1) to (27) in any combination, wherein the anionic exchange column comprises a type 1 or 2 strong base anion resin, and each said anion exchange sites comprise a quaternary amino moiety.

In aspect (29), the present invention provides a process according to any one or more of aspects (1) to (28) in any combination, wherein said separating further comprises passing through the column a regeneration fluid to regenerate the column, the regeneration fluid comprising an anionic regeneration compound selected to replace the anionic contaminant salt attached to the anion exchange sites, wherein the regeneration fluid comprises one or more of sodium hydroxide, sodium carbonate and sodium bicarbonate, or preferably sodium hydroxide at a concentration between about 10 g/L and about 150 g/L, preferably between about 50 g/L and about 100 g/L, or more preferably about 80 g/L.

In aspect (30), the present invention provides a process according to any one or more of aspects (1) to (29) in any combination, wherein the aqueous solution has a carbon dioxide loading capacity between about 0.01 and about 1.0, preferably between about 0.05 and about 0.3, or more preferably between about 0.1 and about 0.15, said loading capacity being obtained from a molar ratio between the carbon dioxide and the amine compound in the aqueous solution, and wherein the aqueous solution has a concentration of the carbamate compound between about 0.5 weight % and about 10 weight %, preferably between about 1.0 weight % and about 8 weight %, or more preferably between about 1.5 weight % and 4.5 weight % with respect to the total weight of the aqueous solution.

In aspect (31), the present invention provides a process according to any one or more of aspects (1) to (30) in any combination, wherein prior to said passing the aqueous solution through the column, the aqueous solution has a temperature between about 10° C. and about 50° C., preferably between about 20° C. and about 40° C., or more preferably between about 30° C. and about 38° C., and optionally is filtered to remove an insoluble precipitate.

In aspect (32), the present invention provides a process according to any one or more of aspects (1) to (31) in any combination, wherein the anionic contaminant salt comprises one or more of a formate salt, an acetate salt, a thiocyanate salt, a thiosulfate salt, a glycolate salt, a chloride salt, an oxalate salt, a butyrate salt, a phosphate salt, a nitrate salt, a propionate salt and a sulfate salt, or preferably a formate salt.

In aspect (33), the present invention provides a process according to any one or more of aspects (1) to (32) in any combination, wherein said passing the extraction fluid through the column is conducted at a pressure between about 0.5 atm and about 20 atm, preferably between about 1 atm and about 15 atm, or more preferably between about 6 atm and about 8 atm.

In aspect (34), the present invention provides a process according to any one or more of aspects (1) to (33) in any combination, wherein the amine compound is one or more of monoethanolamine, 1-amino-2-propanol and 2-amino-2-methyl-1-propanol, or more preferably monoethanolamine.

In aspect (35), the present invention provides a process according to any one or more of aspects (1) to (34) in any combination, wherein the acid compound is carbonic acid.

In aspect (36), the present invention provides a process according to any one or more of aspects (1) to (35) in any combination, wherein the carbonic acid is selected to donate a proton to the carbamate compound attached to the anion exchange sites to form the conjugate acid of the carbamate compound and a bicarbonate ion, and to decompose the conjugate acid of the carbamate compound to the amine compound and the carbon dioxide.

In aspect (37), the present invention provides a process according to any one or more of aspects (1) to (36) in any combination, wherein the separated mixture is a separated aqueous solution having the anionic contaminant salt at a concentration up to about 3 weight %, preferably up to about 1 weight % or more preferably up to about 0.5 weight % with respect to the total weight of the separated aqueous solution.

In aspect (38), the present invention provides a process according to any one or more of aspects (1) to (37) in any combination, wherein the anionic exchange column comprises a type 1 or 2 strong base anion resin, and each said anion exchange sites comprise a quaternary amino moiety.

Additional and alternative features of the present invention will be apparent to a person skilled in the art from the following detailed description of the preferred embodiments thereof.

BRIEF DESCRIPTION OF THE DRAWINGS

Reference may now be had to the following detailed description taken together with the accompanying drawings in which:

FIG. 1 is a flow diagram illustrating a process for extracting an alkanolamine compound and a carbamate compound in accordance with a preferred embodiment of the present invention.

DETAILED DESCRIPTION OF THE PREFERRED EMBODIMENTS

Reference is made to FIG. 1 which shows a schematic of a process in accordance with a preferred embodiment of the present invention, and which incorporates an anion exchange step for treating an alkanolamine solution utilized for absorbing carbon dioxide in a coal burning power plant. As will be described in greater detail below, the process is conducted in a carbon capture apparatus 100 which includes an absorber tower 1, a stripper tower 2 and an anion exchange unit 3, wherein the absorber tower 1, the stripper tower 2 and the anion exchange unit 3 are in fluid communication with one another. The process includes: a chemical absorption step to be performed in the absorber tower 1; a thermal regeneration step to be performed in the stripper tower 2; and the anion exchange step to be performed in the anion exchange unit 3. It is to be appreciated that although the process in accordance with this preferred embodiment is described for application in the coal burning power plant, the process of the present invention is not limited to such application, and may be applied in various other contexts for removing carbon dioxide.

In the chemical absorption step, an exhaust gas stream 4 produced from the coal burning power plant, and which includes a flue gas containing carbon dioxide, as well as other gaseous compounds resulting from combustion of coal is channeled into the absorber tower 1 from a lower portion thereof. The gas stream 4 is contacted in the absorber tower 1 with a lean monoethanolamine stream 5 flown into the absorber tower 1 through an upper portion thereof, so as to effect countercurrent contact between the gas stream 4 and the lean monoethanolamine stream 5. The lean monoethanolamine stream 5 includes monoethanolamine of the formula $HOCH_2CH_2NH_2$ alone or together with other primary or secondary alkanolamine compounds to conduct chemical absorption of carbon dioxide and the other gaseous compounds, such as but not limited to hydrogen sulfide and sulfur dioxide, during the countercurrent contact with the gas stream 4. As will be described in greater detail below, the monoethanolamine stream 5 includes a recycled monoethanolamine stream 6 from the stripper tower 2 and a treated monoethanolamine stream 7 from the anion exchange unit 3. After contact with the exhaust gas stream 4, the lean monoethanolamine stream 5 flows downwardly and out of the absorber tower 1 as a loaded monoethanolamine stream 8 having absorbed carbon dioxide at a carbon dioxide lean loading between 0.05 to 0.3 or preferably between 0.1 and 0.15 (expressed as a molar ratio between the carbon dioxide and monoethanolamine) and the other gaseous compounds.

The exhaust gas stream 4 with carbon dioxide and the other gaseous compounds removed therefrom is vented from the absorber tower 1.

In the thermal regeneration step, the loaded monoethanolamine stream 8 is fed into the stripper tower 2 through an upper portion thereof, and is contacted with a steam (not shown) generated by a stripper tower reboiler (not shown) to remove at least a portion of carbon dioxide and the other gaseous compounds absorbed in the loaded monoethanolamine stream 8. The loaded monoethanolamine stream 8 having contacted the steam leaves the stripper tower 2 as a stripped monoethanolamine stream 9 through a bottom portion of the stripper tower 2. A portion of the stripped monoethanolamine stream 9 is rechanneled as the recycled monoethanolamine stream 6 to form part of the lean monoethanolamine stream 5, and the remaining portion of the stream 9 is flown to the anion exchange unit 3 as a bleed monoethanolamine stream 10 for further treatment.

It is to be appreciated that the thermal regeneration step does not completely remove all carbon dioxide and the other gaseous compounds from the loaded monoethanolamine stream 8, and the stripped monoethanolamine stream 9, as well as the bleed monoethanolamine stream 10, includes some portions of the carbon dioxide and the other gaseous compounds. Furthermore, the bleed monoethanolamine stream 10 also includes a number of contaminants and degradation products which may result from one or both of the chemical absorption and thermal regeneration steps. Such degradation products or corrosive heat stable salts include formate, oxalate, glycolate and/or acetate, and could causes damages to the carbon capture apparatus 100 and various components thereof.

To reduce an amount of the heat stable salts in the bleed monoethanolamine stream 10, in the anion exchange chromatography step the bleed monoethanolamine stream 10 is flown through a type 1 or 2 strong base anion resin (not shown) included in the anion exchange unit 3, and which includes a plurality of anion exchange sites having a positively charged quaternary amino moiety to effect loading or attachment of the heat stable salts thereto. A first effluent eluted from the anion resin by passing the bleed monoethanolamine stream 10 therethrough is channeled towards the absorber tower 1 as the treated monoethanolamine stream 7, and is combined with the recycled monoethanolamine stream 6 to form the lean monoethanolamine stream 5 for continuous cyclic use in contacting the exhaust gas stream 4 in the absorber tower 1. Without wishing to be bound by theory, it is contemplated that some monoethanolamine in the bleed monoethanolamine stream 10 prior to or during passing through the anion resin reacts with carbon dioxide to form the carbamate anion $HOCH_2CH_2NHCOO^-$ according to reaction (1) identified above, and the carbamate anion attaches to the anion exchange sites. The carbamate anion attached to the anion exchange sites and not recovered in the treated monoethanolamine stream 7 could represent a loss of monoethanolamine in the carbon capture apparatus 100 over time, if the attached carbamate anion, together with the attached heat stable salts, is subsequently eluted from the resin during resin regeneration as will be further described below.

To avoid such loss of monoethanolamine in the apparatus 100, the anion resin is contacted with an aqueous carbonic acid stream 11 to selectively remove the carbamate anion from the anion exchange sites and to obtain a second effluent. Without wishing to be bound by theory, it has been envisioned that such selective carbamate anion removal may be described by equation (6):

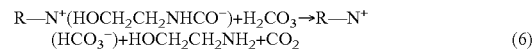

$$R-N^+(HOCH_2CH_2NHCO^-)+H_2CO_3 \rightarrow R-N^+(HCO_3^-)+HOCH_2CH_2NH_2+CO_2 \quad (6)$$

The carbamate anion attached on the resin may behave as a conjugate base to accept a proton from carbonic acid, removing and decomposing the carbamate anion to form monoethanolamine and carbon dioxide. The bicarbonate anion produced from equation (6) may be attached to the anion exchange sites. The acid base reaction in equation (6) is believed to be quite rapid.

It has been appreciated that carbonic acid may be exist in the aqueous stream 11 in chemical equilibrium as described by equation (7):

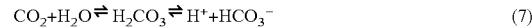

$$CO_2+H_2O \rightleftharpoons H_2CO_3 \rightleftharpoons H^+ + HCO_3^- \quad (7)$$

The bicarbonate anion resulting from the chemical equilibrium of equation (7) or from the acid base reaction of equation (6) may cause removal of for example the heat stable salt formate anion according to equation (8):

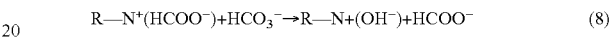

$$R-N^+(HCOO^-)+HCO_3^- \rightarrow R-N+(OH^-)+HCOO^- \quad (8)$$

It has been envisioned however that carbonic acid is only weakly dissociated and consequently the bicarbonate anion concentration is low, making the carbonic acid and the bicarbonate anion a poor regenerant for the heat stable salts attached on the anion resin. Furthermore, possible formation of the conjugate acid forms of the heat stable salts may maintain low solution pH, so as to inhibit further dissociation of the carbonic acid.

It has been further envisioned that as equation (6) is based on acid base neutralization reaction which stoichiometrically consumes the carbonic acid and not just the bicarbonate anion, the reaction identified by equation (6) is not significantly affected by the carbonic acid's dissociation constant or formation of the bicarbonate anion. In the presence of absorbed or dissolved carbon dioxide, any carbonic acid consumed in equation (6) may be replaced by the carbon dioxide reacting with water to produce more carbonic acid in the chemical equilibrium described by equation (7), and therefore, equation (6) in removing the carbamate anion is not limited by the carbonic acid and bicarbonate equilibrium concentration. To drive the chemical equilibrium of equation (7) towards carbonic acid, it is preferred that the aqueous carbonic acid stream 11 is contracted with the anion resin at an elevated pressure, preferably between 1 and 14 atm or more preferably between 6 and 8 atm.

The anion resin is further rinsed with a water stream 12 and the water stream 12 is combined with the second effluent obtained from contacting the carbonic acid stream 11 with the anion resin to form a recovered monoethanolamine stream 13. The recovered monoethanolamine stream 13 is in turn combined with the treated monoethanolamine stream 7 for continuous cyclic use as the lean monoethanolamine stream 5 in contacting the exhaust gas stream 4 in the absorber tower 1.

To regenerate the anion resin, an aqueous sodium hydroxide stream (not shown) is flown through the anion resin to obtain a third effluent containing the heat stable salts removed from the anion exchange sites, and the third effluent is discarded as a waste stream.

In an experimental study, recovery of a carbamate anion from an anion exchange resin was confirmed. In the study, 20 mL of type II anion resin was loaded into a packed resin column, and the resin was converted into the hydroxide form by passing 60 mL of a sodium hydroxide solution with a concentration of 80 g/L through the column. The residual sodium hydroxide was washed from the resin by passing 60 mL of deionized water through the column. A feed solution containing 167 g/L monoethanolamine ("MEA") was prepared by sparging carbon dioxide gas through the feed solution until a steady pH of 10.2 was achieved. The feed solution thus prepared was titrated with 0.1 M NaOH, and found to have a lean loading level of 0.27 mol $CO_2$/mol MEA which is equivalent to 45.8 g MEA/L. Formic acid was then added to the feed solution to give a concentration of 11.2 g/L, which is equivalent to 11 g/L as formate.

200 mL of the feed solution was passed through the packed resin column, and an effluent was collected in a flask. The remaining liquid void in the resin column was displaced by passing air therethrough, and the displaced water was collected into the same flask giving a combined volume of 212 mL. The feed was then rinsed from the resin column with 58 mL of deionized water, and an effluent was collected separately and had a volume of 58 mL. The resin column was then regenerated and rinsed with 60 mL of 80 g/L sodium hydroxide and 50 mL of deionized water. The effluents from both the regeneration and washing steps were collected together giving a combined volume of 110 mL. Quantification of monoethanolamine and formate is summarized in Table 1:

TABLE 1

| Sample | Volume ml | MEA g/L | MEA g | Formate g/L | Formate g |
|---|---|---|---|---|---|
| Feed | 200 | 167 | 33.4 | 11 | 2.2 |
| Feed and air displacement effluent | 212 | 147.8 | 31.3 | 6 | 1.27 |
| Feed rinse effluent | 58 | 22.3 | 1.29 | 1.63 | 0.09 |
| Regenerant and rinse effluent | 110 | 6.13 | 0.67 | 7.69 | 0.85 |

The same experiment was repeated but with inclusion of an additional carbamate rinse step incorporated between the feed rinse and regeneration steps. The carbamate rinse step involved passing 210 mL of carbonic acid at 11 atm through the packed resin column and collecting an effluent. Quantification of monoethanolamine and formate from the repeated experiment is summarized in Table 2:

TABLE 2

| Sample | Volume ml | MEA g/L | MEA g | Formate g/L | Formate g |
|---|---|---|---|---|---|
| Feed | 200 | 167 | 33.4 | 11 | 2.2 |
| Feed and air displacement effluent | 210 | 150.1 | 31.5 | 5.8 | 1.22 |
| Feed rinse effluent | 65 | 21.7 | 1.41 | 1.46 | 0.095 |
| Carbonic acid effluent | 210 | 4.06 | 0.85 | 0.94 | 0.19 |
| Regenerant and rinse effluent | 128 | 0 | 0 | 5 | 0.64 |

Tables 1 and 2 confirmed that with inclusion of the carbonic acid strip step, detectable amounts of monoethanolamine was found in the regenerant and rinse effluent, confirming that the carbamate anion was removed from the resin column in the carbonic acid strip step.

While the invention has been described with reference to preferred embodiments, the invention is not or intended by the applicant to be so limited. A person skilled in the art would readily recognize and incorporate various modifications, additional elements and/or different combinations of the described components consistent with the scope of the invention as described herein.

I claim:

1. A process for separating an amine compound or a conjugate acid thereof and a carbamate compound or a conjugate acid thereof from a mixture having the amine compound, the carbamate compound, carbon dioxide and at least one anionic contaminant salt using an anionic exchange column having a plurality of anion exchange sites,
the amine compound being an optionally substituted piperazine or having formula (1) of $R_{3-x}N(R^1-Q-R^1-OH)_x$ and the carbamate compound being an optionally substituted piperazine carbamate or piperazine dicarbamate, or having formula (2) of $(HO-R^1-Q-R^1)_y NH_{2-y}C(O)O^-$, wherein at least a portion of the carbamate compound is present in the mixture from a reversible reaction between the amine compound and the carbon dioxide to produce the carbamate compound and a hydrogen atom or the conjugate acid of the amine compound, wherein x and y are independently of each other 1 or 2, R is a hydrogen atom or optionally substituted straight or branched $C_1$-$C_8$ alkyl, $R^1$ is nothing or optionally substituted straight or branched $C_1$-$C_4$ alkylene, and Q is nothing, O or S, and wherein the optionally substituted piperazine comprises at least one ring nitrogen atom bonded to a hydrogen atom, at least one R is a hydrogen atom, and at least $R^1$ in each said formulas (1) and (2) is optionally substituted straight or branched $C_1$-$C_4$ alkylene;
wherein the process comprises:
passing the mixture through the column to effect attachment to the at least one anionic contaminant salt to the anion exchange sites, and collecting from the column a first effluent comprising at least the amine compound or the conjugate acid thereof;
passing through the column an extraction fluid at a pressure between 6 atm and 15 atm to obtain a second effluent, the extraction fluid comprising carbonic acid, to effect removal of the carbamate compound attached to the anion exchange sites, wherein the second effluent comprises at least the carbamate compound, the conjugate acid of the carbamate compound or a decomposition product thereof, said decomposition product comprising the amine compound and the carbon dioxide; and
passing through the column a regeneration fluid to regenerate the column, the regeneration fluid comprising an anionic regeneration compound selected to replace the anionic contaminant salt attached to the anion exchange sites,
wherein the first and second effluents are collected to obtain a separated mixture comprising at least the amine compound or the conjugate acid thereof and the carbamate compound or the conjugate acid thereof.

2. The process of claim 1, wherein the process is for use with a method for removing from a gaseous stream carbon dioxide and optionally one or more of hydrogen sulfide, sulfur dioxide, carbonyl sulfide, carbon disulfide, nitrogen dioxide and hydrogen cyanide, said mixture being an aqueous solution obtained from contacting a liquid stream comprising the amine compound with the gaseous stream to obtain a loaded fluid mixture, heating the loaded fluid mixture with a steam to remove at least a portion of the gaseous stream absorbed in the loaded fluid mixture to obtain a heated fluid mixture, and refluxing the heated fluid mixture to obtain the aqueous solution.

3. The process of claim 2, wherein the aqueous solution has a carbon dioxide loading capacity between about 0.01 and about 1.0, said loading capacity being obtained from a molar ratio between the carbon dioxide and the amine compound in the aqueous solution, and wherein the aqueous solution has a concentration of the carbamate compound between about 0.5 weight % and about 10 weight % with respect to the total weight of the aqueous solution.

4. The process of claim 2, wherein at least a portion of the at least one anionic contaminant salt is produced during one or both of said contacting the liquid stream with the gaseous stream and said heating the loaded fluid mixture with the steam, said at least one anionic contaminant salt being a heat stable salt comprising one or more of a formate salt, an acetate salt, a thiocyanate salt, a thiosulfate salt, a glycolate salt, a chloride salt, an oxalate salt, a butyrate salt, a phosphate salt, a nitrate salt, a propionate salt and a sulfate salt.

5. The process of claim 1, wherein the amine compound is one or more of monoethanolamine, diethanolamine, monoisopropanolamine, diisopropanolamine, 1-amino-2-propanol, 2-amino-2-methyl-1-propanol, 2-amino-2-methyl-1,3-propanediol, N-methylmonoethanolamine, N-ethylmonoethanolamine, N-butylmonoethanolamine, 2-(2-aminoethoxy)ethanol, N-(2-hydroxyethyl)ethylenediamine, piperazine, 1-[2-(2-Hydroxyethoxy)ethyl]piperazine, 1-methylpiperazine, 1-(2-methoxyethyl)piperazine, 1-(2-hydroxyethyl)piperazine, 1-(2-ethoxyethyl)piperazine and 1-(2-aminoethyl)piperazine.

6. The process of claim 1, wherein the carbonic acid donates a proton to the carbamate compound attached to the anion exchange sites to form the conjugate acid of the carbamate compound and optionally decomposes the conjugate acid of the carbamate compound to form the amine compound, thereby removing the carbamate compound from the anion exchange sites.

7. The process of claim 1, wherein the amine compound has formula (3) $HO-R^2-NH_2$, $R^2$ being $C_1$-$C_8$ alkylene, and the reversible reaction is $2\ HO-R^2-NH_2+CO_2 \rightleftharpoons HO-R^2-NH_3^+ + HO-R^2-NH-COO^-$, and wherein, the carbonic acid donates a proton to $HO-R^2-NH-COO^-$ attached to the anion exchange sites to form $HO-R^2-NH-COOH$ and a bicarbonate ion, and optionally decomposes $HO-R^2-NH-COOH$ to $HO-R^2-NH_2$ and $CO_2$.

8. The process of claim 1, wherein the regeneration fluid is an aqueous solution comprising one or more of sodium hydroxide, sodium carbonate and sodium bicarbonate at a concentration between about 10 g/L and about 150 g/L.

9. The process of claim 1, wherein the separated mixture is a separated aqueous solution having the at least one anionic contaminant salt at a concentration up to about 3 weight % with respect to the total weight of the separated aqueous solution.

10. The process of claim 1, wherein the anionic exchange column comprises a type 1 or 2 strong base anion resin, and each said anion exchange sites comprise a quaternary amino moiety.

11. A process for separating an amine compound or a conjugate acid thereof and a carbamate compound or a conjugate acid thereof from a mixture having the amine compound, the carbamate compound, carbon dioxide and at least one anionic contaminant salt using an anionic exchange column having a plurality of anion exchange sites,
the amine compound being an optionally substituted piperazine or having formula (1) of $R_{3-x}N(R^1$-$Q$-$R^1$-$OH)_x$ and the carbamate compound being an optionally substituted piperazine carbamate or piperazine dicarbamate, or having formula (2) of $(HO-R^1$-$Q$-$R^1)_y NH_{2-y}C(O)O^-$, wherein x and y are independently of each other 1 or 2, R is a hydrogen atom or optionally substituted straight or branched $C_1$-$C_8$ alkyl, $R^1$ is nothing or optionally substituted straight or branched $C_1$-$C_4$ alkylene, and Q is nothing, O or S, and wherein the optionally substituted piperazine comprises at least one ring nitrogen atom bonded to a hydrogen atom, at least one R is a hydrogen atom, and at least $R^1$ in each said formulas (1) and (2) is optionally substituted straight or branched $C_1$-$C_4$ alkylene;
wherein the process comprises:
passing the mixture through the column to effect attachment of the at least one anionic contaminant salt to the anion exchange sites, and collecting from the column a first effluent comprising at least the amine compound or the conjugate acid thereof;
passing through the column an extraction fluid at a pressure between 6 atm and 15 atm to obtain a second effluent, the extraction fluid comprising carbonic acid, to effect removal of the carbamate compound attached to the anion exchange sites, wherein the second effluent comprises at least the carbamate compound, the conjugate acid of the carbamate compound or a decomposition product thereof, said decomposition product comprising the amine compound and the carbon dioxide; and
passing through the column a regeneration fluid to regenerate the column, the regeneration fluid comprising an anionic regeneration compound selected to replace the anionic contaminant salt attached to the anion exchange sites,
wherein the first and second effluents are collected to obtain a separated mixture comprising at least the amine compound or the conjugate acid thereof and the carbamate compound or the conjugate acid thereof.

12. The process of claim 11, wherein the carbonic acid donates a proton to the carbamate compound attached to the anion exchange sites to form the conjugate acid of the carbamate compound, thereby removing the carbamate compound from the anion exchange sites.

13. The process of claim 11, wherein the process is for use with a method for removing from a gaseous stream carbon dioxide and optionally one or more of hydrogen sulfide, sulfur dioxide, carbonyl sulfide, carbon disulfide, nitrogen dioxide and hydrogen cyanide, said mixture being an aqueous solution obtained from contacting a liquid stream comprising the amine compound with the gaseous stream to obtain a loaded fluid mixture, heating the loaded fluid mixture with a steam to remove at least a portion of the gaseous stream absorbed in the loaded fluid mixture to obtain a heated fluid mixture, and refluxing the heated fluid mixture to obtain the aqueous solution.

14. The process of claim 13, wherein the aqueous solution has a carbon dioxide loading capacity between about 0.01 and about 1.0, said loading capacity being obtained from a molar ratio between the carbon dioxide and the amine compound in the aqueous solution, and wherein the aqueous solution has a concentration of the carbamate compound between about 0.5 weight % and about 10 weight % with respect to the total weight of the aqueous solution.

15. The process of claim 13, wherein at least a portion of the at least one anionic contaminant salt is produced during one or both of said contacting the liquid stream with the gaseous stream and said heating the loaded fluid mixture with the steam, said at least one anionic contaminant salt being a heat stable salt comprising one or more of a formate salt, an acetate salt, a thiocyanate salt, a thiosulfate salt, a glycolate salt, a chloride salt, an oxalate salt, a butyrate salt, a phosphate salt, a nitrate salt, a propionate salt and a sulfate salt.

16. The process of claim 11, wherein the amine compound is one or more of monoethanolamine, diethanolamine, monoisopropanolamine, diisopropanolamine, 1-amino-2-propanol, 2-amino-2-methyl-1-propanol, 2-amino-2-methyl-1,3-propanediol, N-methylmonoethanolamine, N-ethylmonoethanolamine, N-butylmonoethanolamine, 2-(2-aminoethoxy)ethanol, N-(2-hydroxyethyl)ethylenediamine, piperazine, 1-[2-(2-Hydroxyethoxy)ethyl]piperazine, 1-methylpiperazine, 1-(2-methoxyethyl)piperazine, 1-(2-hydroxyethyl)piperazine, 1-(2-ethoxyethyl)piperazine and 1-(2-aminoethyl)piperazine.

17. The process of claim 11, wherein at least a portion of the carbamate compound is present in the mixture from a reversible reaction between the amine compound and the carbon dioxide to produce the carbamate compound and a hydrogen atom or the conjugate acid of the amine compound, and the amine compound has formula (3) $HO-R^2-NH_2$, $R^2$ being $C_1$-$C_8$ alkylene, wherein the reversible reaction is $2\ HO-R^2-NH_2 + CO_2 \rightleftharpoons HO-R^2-NH_3^+ + HO-R^2-NH-COO^-$, and the carbonic acid donates a proton to $HO-R^2-NH-COO^-$ attached to the anion exchange sites to form $HO-R^2-NH-COOH$ and a bicarbonate ion, and optionally decomposes $HO-R^2-NH-COOH$ to $HO-R^2-NH_2$ and $CO_2$.

18. The process of claim 11, wherein the regeneration fluid is an aqueous solution comprising one or more of sodium hydroxide, sodium carbonate and sodium bicarbonate, at a concentration between about 10 g/L and about 150 g/L.

19. The process of claim 11, wherein the separated mixture is a separated aqueous solution having the at least one anionic contaminant salt at a concentration up to about 3 weight %, with respect to the total weight of the separated aqueous solution.

20. The process of claim 11, wherein the anionic exchange column comprises a type 1 or 2 strong base anion resin, and each said anion exchange sites comprise a quaternary amino moiety.

21. The process of claim 1, wherein the amine compound is monoethanolamine.

22. The process of claim 11, wherein the amine compound is monoethanolamine.

* * * * *